United States Patent
Gloss et al.

(10) Patent No.: US 9,375,311 B2
(45) Date of Patent: Jun. 28, 2016

(54) PROSTHETIC VALVES AND ASSOCIATED APPARTUSES, SYSTEMS AND METHODS

(71) Applicant: Medtronic, Inc., Minneapolis, MN (US)

(72) Inventors: Michael Gloss, Minneapolis, MN (US); Timothy Groen, Rush City, CA (US); Carolyn Majkrzak, Chanhassen, MN (US); Matthew Rust, Windsor, CA (US); Timothy Ryan, Shorewood, MN (US); Matthew Weston, Roseville, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/268,494

(22) Filed: May 2, 2014

(65) Prior Publication Data

US 2014/0330371 A1    Nov. 6, 2014

Related U.S. Application Data

(60) Provisional application No. 61/819,486, filed on May 3, 2013, provisional application No. 61/930,912, filed on Jan. 23, 2014.

(51) Int. Cl.
*A61F 2/24* (2006.01)
*A61F 2/82* (2013.01)
*A61F 2/07* (2013.01)

(52) U.S. Cl.
CPC ............. *A61F 2/2418* (2013.01); *A61F 2/07* (2013.01); *A61F 2/24* (2013.01); *A61F 2/82* (2013.01); *A61F 2220/0075* (2013.01); *A61F 2250/0039* (2013.01)

(58) Field of Classification Search
CPC .......... A61F 2/07; A61F 2/24; A61F 2/2418; A61F 2/82; A61F 2250/0037; A61F 2250/0039
USPC ................................................. 623/2.14, 2.17
See application file for complete search history.

(56) References Cited

U.S. PATENT DOCUMENTS

| | | | |
|---|---|---|---|
| 2010/0049313 A1* | 2/2010 | Alon | A61F 2/2418 623/2.11 |
| 2010/0100176 A1 | 4/2010 | Elizondo et al. | |
| 2010/0168844 A1 | 7/2010 | Toomes et al. | |

(Continued)

FOREIGN PATENT DOCUMENTS

| | | |
|---|---|---|
| WO | WO2009/045338 | 4/2009 |
| WO | WO2012/032187 | 3/2012 |

OTHER PUBLICATIONS

PCT/US2014/036709, International Search Report and Written Opinion, mailed Jul. 31, 2014.

*Primary Examiner* — David Isabella
*Assistant Examiner* — Dinah Baria

(57) ABSTRACT

A valve prosthesis includes an expandable frame. The expandable frame has an outflow portion and an inflow portion connected to the outflow portion. The frame defines a central lumen extending between the outflow portion and the inflow portion. The frame is generally cylindrical in a fully expanded configuration. When the frame is in the fully expanded configuration, an outer surface of the inflow portion is concave. The inflow portion has an upper inflow portion and a lower inflow portion. When the frame is in the fully expanded configuration, the upper inflow portion flares outwardly from the central lumen of the frame to greater extent than the lower inflow portion.

17 Claims, 22 Drawing Sheets

(56) References Cited

U.S. PATENT DOCUMENTS

| | | |
|---|---|---|
| 2010/0249923 A1 | 9/2010 | Alkhatib et al. |
| 2011/0022157 A1 | 1/2011 | Essinger et al. |
| 2012/0165544 A1 | 6/2012 | Dochnahl et al. |
| 2012/0271398 A1 | 10/2012 | Essinger et al. |

\* cited by examiner

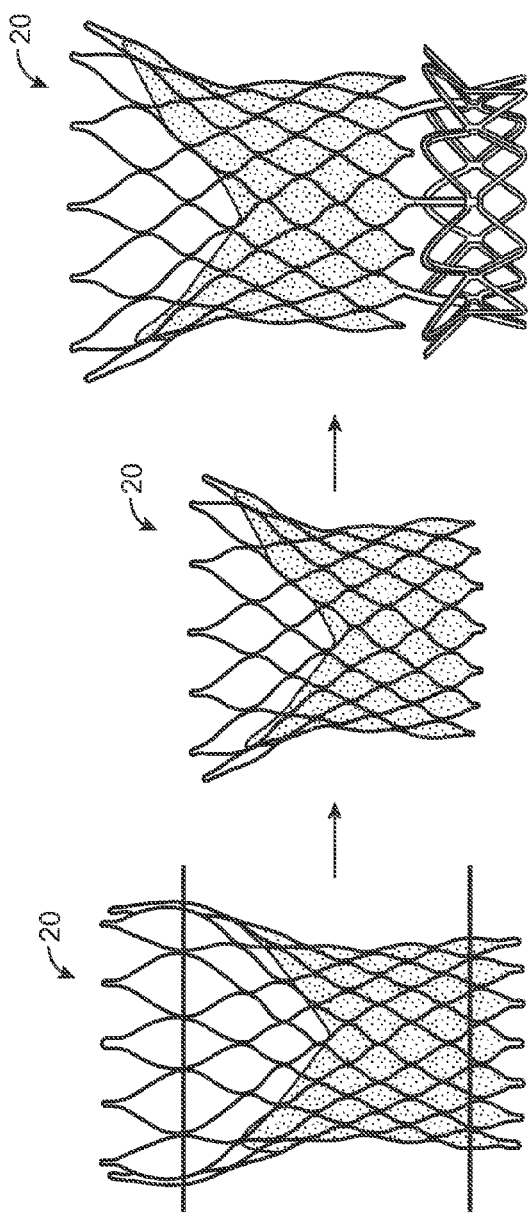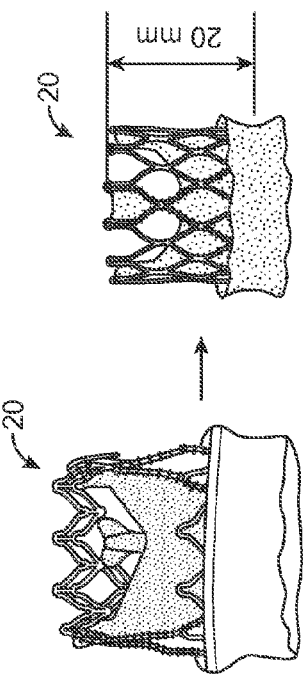
FIG. 13A  FIG. 13B  FIG. 13C
FIG. 14A  FIG. 14B

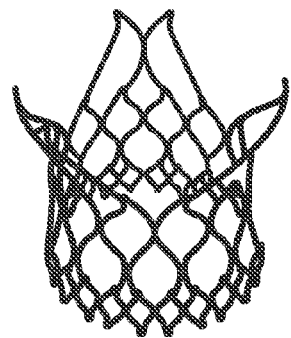
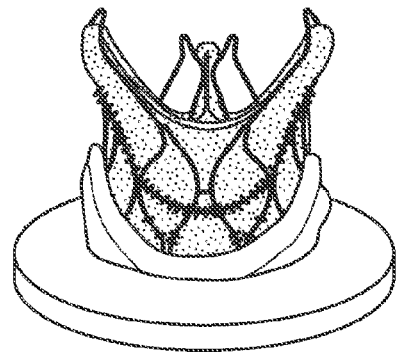
FIG. 26A    FIG. 26B
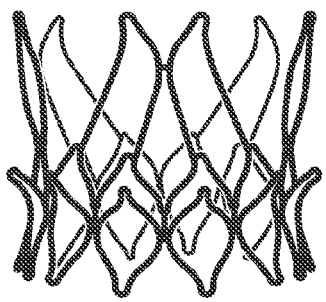
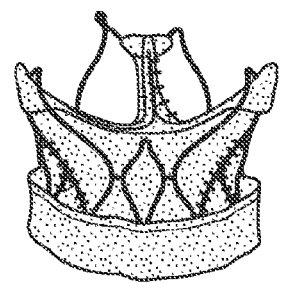
FIG. 27A    FIG. 27B
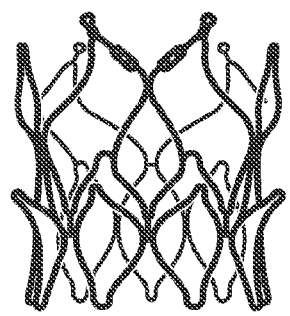
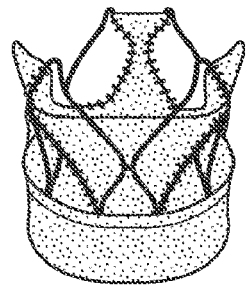
FIG. 28A    FIG. 28B

PROSTHETIC VALVES AND ASSOCIATED APPARTUSES, SYSTEMS AND METHODS

RELATED APPLICATIONS

This application claims the benefit of U.S. Provisional Patent Application No. 61/819,486, filed on May 3, 2013, and U.S. Provisional Patent Application No. 61/930,912, filed on Jan. 23, 2014, each of which Provisional patent applications are hereby incorporated herein by reference in their respective entireties to the extent that they do not conflict with the disclosure presented herein.

FIELD

The present disclosure relates to, among other things, prosthetic heart valves, and associated apparatuses and methods of use, manufacture and treatment.

BACKGROUND

The transport of vital fluids in the human body is largely regulated by valves. Physiological valves are designed to prevent the backflow of bodily fluids, such as blood, lymph, urine, bile, etc., thereby keeping the body's fluid dynamics unidirectional for proper homeostasis. For example, venous valves maintain the upward flow of blood, particularly from the lower extremities, back toward the heart, while lymphatic valves prevent the backflow of lymph within the lymph vessels, particularly those of the limbs.

A human heart includes four cardiac valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart.

Because of their common function, valves share certain anatomical features despite variations in relative size. Cardiac valves are among the largest valves in the body with diameters that may exceed 30 mm, while valves of smaller veins may have diameters no larger than a fraction of a millimeter. Regardless of their size, however, some physiological valves are situated in specialized anatomical structures known as sinuses. Valve sinuses can be described as dilations or bulges in the vessel wall that houses the valve. The geometry of the sinus has a function in the operation and fluid dynamics of the valve. One function is to guide fluid flow so as to create eddy currents that prevent the valve leaflets from adhering to the wall of the vessel at the peak of flow velocity, such as during systole. Another function of the sinus geometry is to generate currents that facilitate the precise closing of the leaflets at the beginning of backflow pressure. The sinus geometry is also important in reducing the stress exerted by differential fluid flow pressure on the valve leaflets or cusps as they open and close.

Sinuses of the pulmonary trunk comprise the space at the origin of the pulmonary trunk between the dilated wall of the vessel and each cusp of the pulmonic valve. Aortic sinuses or Valsalva sinuses comprise the space between the superior aspect of each cusp of the aortic valve and the dilated portion of the wall of the ascending aorta, immediately above each cusp. Thus, for example, eddy currents occurring within sinuses of Valsalva in the natural aortic root have been shown to be important in creating smooth, gradual and gentle closure of the aortic valve at the end of systole. Blood is permitted to travel along the curved contour of the sinus and onto the valve leaflets to effect their closure, thereby reducing the pressure that would otherwise be exerted by direct fluid flow onto the valve leaflets. The sinuses of Valsalva also contain the coronary ostia, which are outflow openings of the arteries that feed the heart muscle. When valve sinuses contain such outflow openings, they serve the additional purpose of providing blood flow to such vessels throughout the cardiac cycle.

When valves exhibit abnormal anatomy and function as a result of valve disease or injury, the unidirectional flow of the physiological fluid they are designed to regulate is disrupted, resulting in increased hydrostatic pressure. For example, venous valvular dysfunction leads to blood flowing back and pooling in the lower legs, resulting in pain, swelling and edema, changes in skin color, and skin ulcerations that can be extremely difficult to treat. Lymphatic valve insufficiency can result in lymphedema with tissue fibrosis and gross distention of the affected body part. Cardiac valvular disease may lead to pulmonary hypertension and edema, atrial fibrillation, and right heart failure in the case of mitral and tricuspid valve stenosis; or pulmonary congestion, left ventricular contractile impairment and congestive heart failure in the case of mitral regurgitation and aortic stenosis. Regardless of their etiology, all valvular diseases result in either stenosis, in which the valve does not open properly, impeding fluid flow across it and causing a rise in fluid pressure, or insufficiency/regurgitation, in which the valve does not close properly and the fluid leaks back across the valve, creating backflow. Some valves are afflicted with both stenosis and insufficiency, in which case the valve neither opens fully nor closes completely.

Because of the potential severity of the clinical consequences of valve disease, numerous surgical techniques have been developed to repair a diseased or damaged heart valve. For example, these surgical techniques may include annuloplasty (contracting the valve annulus), quadrangular resection (narrowing the valve leaflets), commissurotomy (cutting the valve commissures to separate the valve leaflets), or decalcification of valve and annulus tissue. Alternatively, the diseased heart valve may be replaced by a prosthetic valve. Where replacement of a heart valve is indicated, the dysfunctional valve is typically removed and replaced with either a mechanical or tissue valve.

In the past, one common procedure has been an open-heart type procedure. However, open-heart valve repair or replacement surgery is a long and tedious procedure and involves a gross thoracotomy, usually in the form of a median sternotomy. In this procedure, a saw or other cutting instrument is used to cut the sternum longitudinally and the two opposing halves of the anterior or ventral portion of the rib cage are spread apart. A large opening into the thoracic cavity is thus created, through which the surgeon may directly visualize and operate upon the heart and other thoracic contents. The patient must typically be placed on cardiopulmonary bypass for the duration of the surgery.

Minimally invasive valve replacement procedures have emerged as an alternative to open-chest surgery. Minimally invasive medical procedures may be considered as procedures that are carried out by entering the body through the skin or through a body cavity or anatomical opening, while minimizing damage to these structures. Two types of minimally invasive valve procedures that have emerged are percutaneous valve procedures and trans-apical valve procedures. Percutaneous valve procedures pertain to making small incisions in the skin to allow direct access to peripheral vessels or body channels to insert catheters. Trans-apical valve procedures pertain to making a small incision in or near the apex of a heart to allow valve access.

While a number of replacement valves, deployment systems, etc. are available, many suffer from one or more drawbacks. Accordingly, additional or improved replacement valves, deployment systems, etc. would be desirable.

SUMMARY

Disclosed herein, among other things, are prosthetic valves and frames for prosthetic valves designed to meet one or more of the following objectives: (i) durability the same or better than convention replacement valves, (ii) valve in valve suitability, (iii) hemodynamics the same or better than conventional valves, (iv) reproducible minimally invasive procedure, (v) ease of implant, (vi) first time deployment accuracy, (vii) reduced cardiopulmonary bypass (CPB) and cross clamp times, (viii) reduced complications and improved safety, and (ix) improved implantability.

Additional design considerations that some embodiments of the replacement valve support structures (or "frames") disclosed herein strive to achieve are: (i) frame height suitable to accommodate aortotomy two centimeters above sinotubular junction (STJ) maximum height, while being as short as possible; (ii) avoidance of crown-like structure/rail in outflow; (iii) maintain access to coronaries; (iv) active fixation in inflow as part of frame; (v) frame depth preferably does not sit lower than four to six millimeters below annulus; and (vi) stabilization feature.

Additional design considerations that some embodiments of valves disclosed herein strive to achieve are: (i) supra-annular attachment of valve in frame; (ii) scalloped inflow; (iii) bovine, porcine or equine pericardium; and (iv) minimize crimping impact on valve tissue.

While not every replacement valve system described herein meets every design consideration outlined above, some functional highlights of the replacement valve systems will be discussed when describing the systems.

In some embodiments, the replacement valve systems described herein are sutureless valve systems. Of course, sutures may be used with such systems. Advantages to sutureless replacement valve systems include shorter implant procedure times and less invasive implantation. Some disadvantages or perceived disadvantages with current sutureless valve systems include potential increased risk of paravalvular leakage (PVL) and potential lack of durability. The designs presented herein preferably address one or more of the disadvantages or perceived disadvantages of current sutureless valve designs.

In some embodiments, a prosthetic valve includes an expandable frame comprising an outflow portion and an inflow portion connected to the outflow portion. The frame defines a central lumen extending between the outflow portion and the inflow portion. The frame is generally cylindrical in a fully expanded configuration. When the frame is in a fully expanded configuration, an outer surface of the inflow portion is concave. The concave nature of the inflow portion of the frame allows the prosthesis to engage an annulus of a valve of a patient and to retain the prosthesis in a desired implant orientation and/or position. The inflow portion of the frame has an upper inflow portion and a lower inflow portion. When the frame is in the fully expanded configuration, the upper inflow portion may flare outwardly from the central lumen of the frame to greater extent than the lower inflow portion. The frame may comprise a plurality of wire enclosed wire formed cells interconnected with one another.

In some embodiments, a prosthetic valve includes an expandable frame comprising an outflow portion and an inflow portion connected to the outflow portion. The frame defines a central lumen extending between the outflow portion and the inflow portion. The frame is generally cylindrical in a fully expanded configuration. The outflow portion of the frame has an upper portion flared inwardly towards the central lumen. The frame may comprise a plurality of wire enclosed wire formed cells interconnected with one another.

One or more embodiments of prosthetic valves and valve frames described herein may have one or more advantages relative to currently existing prosthetic valves or frames. For example, one of more of the embodiments of prosthetic valves and valve frames described herein may achieve one or more of the objectives described above. Such advantages, as well as other advantages, will be apparent to those of skill in the art upon reading this disclosure and reviewing the accompanying drawings.

BRIEF DESCRIPTION OF THE DRAWINGS

FIGS. 10-17 are schematic drawings of frames or prosthetic valves according to various embodiments described herein.

FIGS. 20-36 are schematic drawings of prototype frames or prosthetic valves according to various embodiments described herein.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

The present disclosure relates to prosthetic valves, such as heart valves, and methods, systems, and devices associated therewith. One or more embodiments of the prosthetic valves achieve one or more of the following objectives: (1) durability the same or better than convention replacement valves; (2) valve in valve suitability; (3) hemodynamics the same or better than conventional valves; (4) reproducible minimally invasive procedure; (5) ease of implant; (6) first time deployment accuracy; and (7) reduced cardiopulmonary bypass (CPB) and cross clamp times; (8) reduced complications and improved safety; and (9) improved implantability.

In some embodiments, a prosthetic valve described herein has one or more of the following features: (1) frame height suitable to accommodate aortotomy two centimeters above STJ maximum height, while being as short as possible; (2) avoidance of crown-like structure/rail in outflow; (3) maintain access to coronaries; (4) active fixation in inflow as part of frame; (5) frame depth preferably does not sit lower than four to six millimeters below annulus; and (6) stabilization feature.

In some embodiments, prosthetic valves disclosed herein incorporate one or more of the following design considerations: (1) supra-annular attachment of replacement valve in frame; (2) scalloped inflow; (3) bovine, porcine or equine pericardium; and (4) minimize crimping impact on valve tissue.

Prior to describing various aspects of prosthetic valves or frames that achieve one or more of such objectives or that incorporate one or more of such features or design considerations, a general description of heart valve device components and heart valve anatomy is provided with regard to FIGS. 1-8 (which may, in various aspects, include a discussion of such objectives, features or design considerations).

Figure 1A:
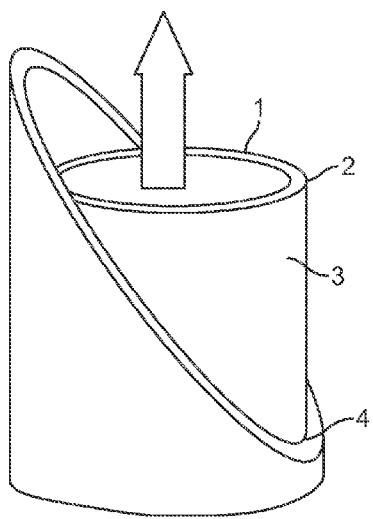
FIG. 1A is a schematic drawing of an exemplary valve in an open position during peak flow.
Figure 1B:
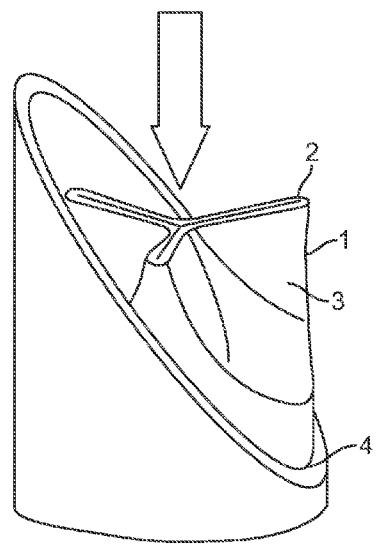
FIG. 1B is a schematic drawing of the valve of FIG. 1A in a closed position to prevent backflow of the fluid across the valve.

FIGS. 1A and 1B generally illustrate an example of a heart valve 1. As illustrated in FIG. 1, valve 1 includes a distal outflow end 2, a plurality of leaflets 3, and a proximal inflow end 4. A typical valve functions similar to a collapsible tube in that it opens widely during systole or in response to muscular contraction to enable unobstructed forward flow across the valvular orifice, as illustrated in FIG. 1A. In contrast, as forward flow decelerates at the end of systole or contraction, the walls of the tube are forced centrally between the sites of attachment to the vessel wall and the valve closes completely as illustrated in FIG. 1B.

Figure 2A:
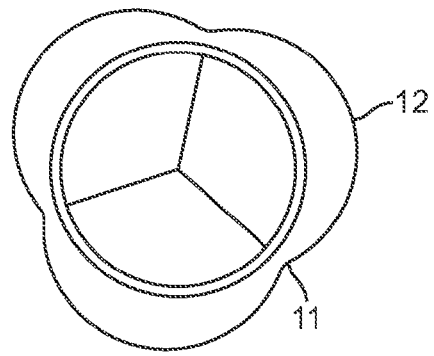
FIG. 2A is a schematic drawing of a top view ill illustrating the anatomy of a typical aortic valve.
Figure 2B:
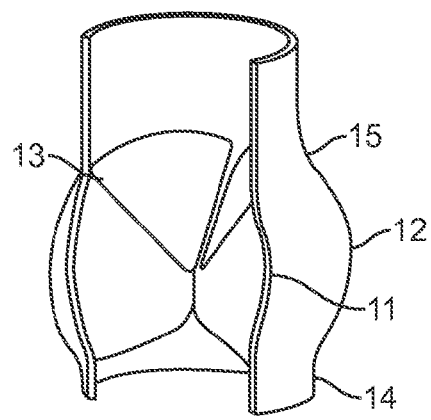
FIG. 2B is a schematic drawing of a cross-sectional view of the aortic valve of FIG. 2A.
Figure 2C:
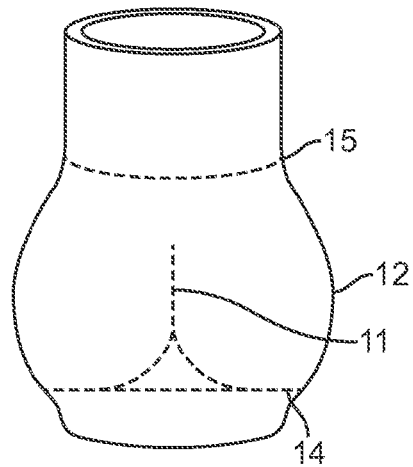
FIG. 2C is a schematic perspective view of the aortic valve of FIG. 2A showing the inflow end, outflow end, and commissures in phantom lines.

FIGS. 2A, 2B, and 2C illustrate the anatomy of a typical aortic valve. In particular, FIG. 2A shows a top view of a closed valve with three valve sinuses, FIG. 2B shows a perspective sectional view of the closed valve, and FIG. 2C shows a view from outside the vessel wall.

One consideration in the design of valve replacement systems and devices is the architecture of the valve to be replaced. For example, mitral and tricuspid heart valves do not have valve sinuses whereas aortic and pulmonic heart valves have valve sinuses. Valve sinuses 12 are dilations of the vessel wall that surround the natural valve leaflets. Typically in the aortic valve, each natural valve leaflet has a separate sinus bulge 12 or cavity that allows for maximal opening of the leaflet at peak flow without permitting contact between the leaflet and the vessel wall. As illustrated in FIGS. 2A, 2B, and 2C, the extent of the sinus 12 is generally defined by the commissures 11, vessel wall 13, inflow end 14, and outflow end 15. The proximal intersection between the sinus cavities define the commissures 11.

FIGS. 2B and 2C also show the narrowing diameter of the sinuses at both inflow end 14 and outflow end 15, thus forming the inflow and outflow annuli of the sinus region. Thus, the valve sinuses form a natural compartment to support the operation of the valve by preventing contact between the leaflets and the vessel wall, which, in turn, may lead to adherence of the leaflets and/or result in detrimental wear and tear of the leaflets. The valve sinuses are also designed to share the stress conditions imposed on the valve leaflets during closure when fluid pressure on the closed leaflets is greatest. The valve sinuses further create favorable fluid dynamics through currents that soften an otherwise abrupt closure of the leaflets under conditions of high backflow pressure. Lastly, the sinuses ensure constant flow to any vessels located within the sinus cavities.

Figure 3:
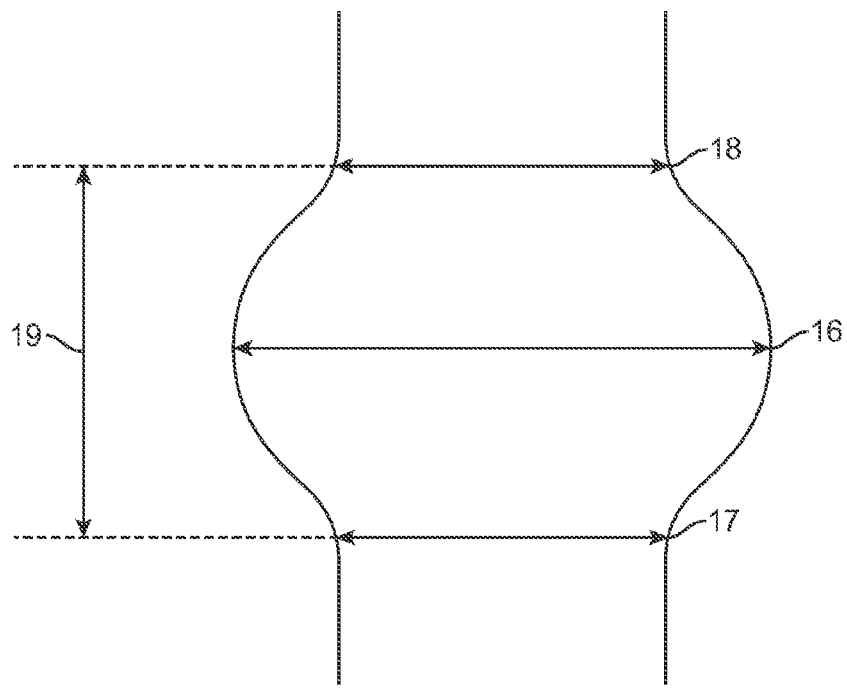
FIG. 3 is a schematic representation of the geometry and relative dimensions of the valve sinus region.

FIG. 3 is a schematic representation of the geometry and relative dimensions of the valve sinus region. As shown in FIG. 3, the valve sinus region is characterized by certain relative dimensions which remain substantially constant regardless of the actual size of the sinuses. Generally, the diameter of the sinus is at its largest at the center of the sinus cavities 16, while there is pronounced narrowing of the sinus region at both the inflow annulus 17 near the inflow end 14 and the outflow annulus 18 near the outflow end 15. Furthermore, the height of the sinus 19 (i.e. the distance between inflow annulus 17 and outflow annulus 18) remains substantially proportional to its overall dimensions. It is thus apparent that the sinus region forms an anatomical compartment with certain constant features that are uniquely adapted to house a valve. The systems and devices disclosed herein may be designed to utilize these anatomical features of the native sinus region for replacement valve function and positioning.

Figure 4:
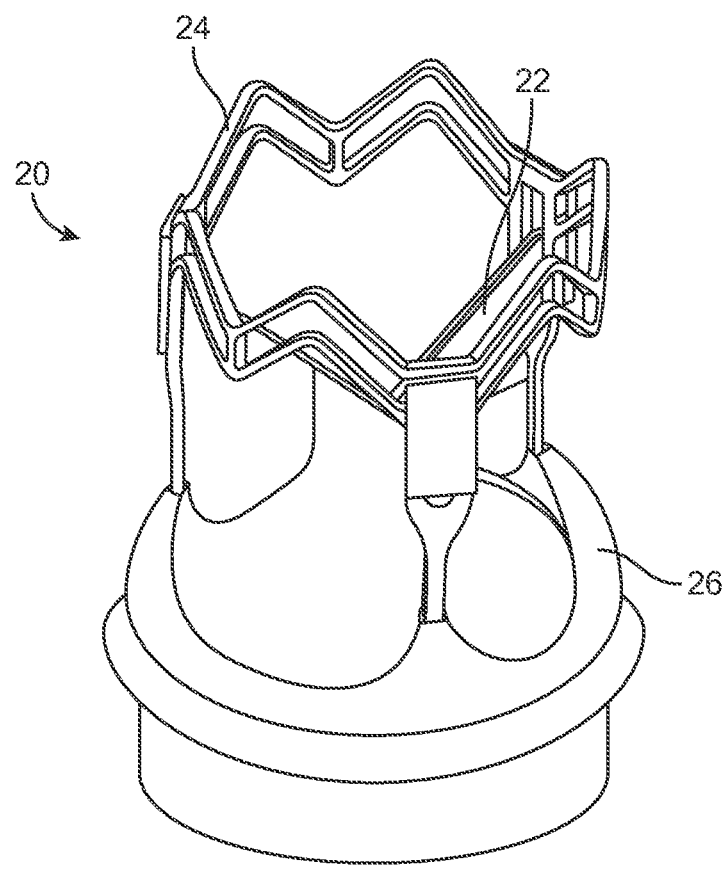
FIG. 4 is a schematic perspective view of a valve replacement system, which includes a replacement valve, a valve support structure (or "frame"), and a valve cuff.

FIG. 4 is a perspective view of a valve replacement system 20 described in more detail in US Published Patent Application No. 2010/0168844 (which application is hereby incorporated by reference in its entirety to the extent that it does not conflict with the disclosure presented herein), which contains general features of the valves described in more detail herein below. Such valves, as well as the valve depicted in FIG. 4, include replacement valve 22, valve support structure or frame 24, and valve cuff 26. Replacement valve 22 may be attached to frame 24 such that replacement valve 22 resides within the support structure. Frame 24 may be, for example, an expandable and collapsible stent-like structure adapted to be delivered to an implantation site such as a native heart valve. Frame 24 may be either self-expanding or non-self-expanding, and may be delivered to the target site via any suitable delivery means as will be appreciated by one skilled in the art. Valve cuff 26 is attachable to the inflow end of replacement valve 22, and may be structured to reduce paravalvular leakage around the valve, as well as to reduce migration and increase stability of replacement valve 22 after implantation at the implantation site.

Valve cuff 26 may include a skirt (not shown in FIG. 4). The skirt may be structured to cover the outer surface of frame 24, such as along the proximal inflow end. In particular, the skirt may wrap around the entire circumference of frame 24 near the proximal inflow end and inflow rim. Furthermore, the skirt may have a generally scalloped configuration so as to substantially align with the scallops found in or around the native valve implantation site and with the scalloped configuration of valve 22. However, one skilled in the art will appreciate that valve cuffs with non-scalloped skirts are also contemplated and within the intended scope of the present disclosure.

In some embodiments, an adhesive may be applied to the valve cuff prior to implantation within a native valve annulus. For example, any suitable biocompatible adhesive may be applied to the outer surfaces of skirt to help seal valve cuff to the surrounding tissue of the valve annulus. While not a necessary component, biocompatible adhesives may help to provide a tighter seal in order to further reduce paravalvular leakage.

In some embodiments, the skirt is formed from a cloth or fabric material. The fabric may comprise any suitable material including, but not limited to, woven polyester such as polyethylene terepthalate, polytetrafluoroethylene (PTFE), or other biocompatible material.

In one exemplary embodiment of assembling valve replacement system, a skirt may initially be positioned around and coupled to the frame in any suitable manner, such as by suturing. The skirt, which is positioned circumferentially around inflow rim of frame, may be wrapped around the proximal inflow end of replacement valve and attached to the valve with, for example, sutures. The foregoing represents only one exemplary embodiment of a method of assembling a valve replacement system in accordance with the present disclosure. Thus, modifications may be made to the number and order of steps as will be appreciate by one skilled in the art.

Replacement valve 22 illustrated in FIG. 4 is a tri-leaflet valve. For purposes of example and not limitation, the following discussion will reference only valve 22, it being understood that any stented or stentless replacement valve is contemplated. Similarly, although frame 24 is shown as structured to receive a tri-leaflet valve, those skilled in the art will appreciate that replacement valves having a number of leaflets other than three will correspondingly require a different valve support structure.

Figure 5:
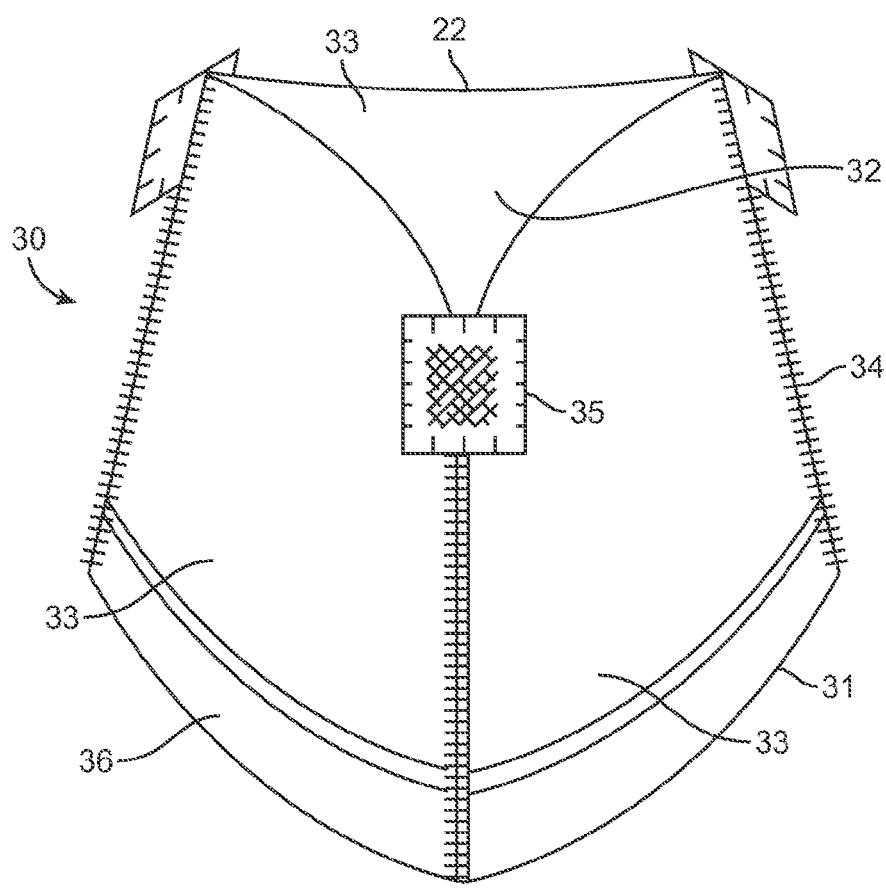
FIG. 5 is a schematic perspective view of the valve of FIG. 4.

FIG. 5 is a perspective view of replacement valve 22, which represents one exemplary embodiment of a tri-leaflet replacement valve useable with valve replacement systems 20 described herein. Replacement valve 22 includes valve body 30 having proximal inflow end 31 and a distal outflow end 32. Valve body 30 includes a plurality of valve tissue leaflets 33 joined by seams 34, wherein each seam 34 is formed by a junction of two leaflets 33. A commissural tab region 35 extends from each seam 34 at the distal end of valve body 30. Inflow end 31 of valve body 30 includes a peripheral edge that may be scalloped or straight. In addition, inflow end 31 of valve body 30 may further comprise reinforcement structure 36 that may be stitched or otherwise attached thereto.

The valve replacement systems and devices described herein are not limited, however, to the specific valve illustrated in FIG. 5. For example, although the proximal inflow end 31 of valve body 30 is shown in FIG. 2 with a scalloped peripheral edge, other shapes and configurations are contemplated and within the intended scope of the present disclosure.

Valve leaflets 33 may be constructed of any suitable material, including but not limited to polymeric materials, metallic materials, and/or tissue-engineered materials. For example, bovine, porcine, equine, ovine, and/or other suitable animal tissues may be used to construct valve leaflets. In some embodiments, valve leaflets may be constructed of or formed from material obtained from, for example, heart valves, aortic roots, aortic walls, aortic leaflets, pericardial tissue, blood vessels, intestinal submucosal tissue, umbilical tissue and the like from humans or animals. In some embodiments, valve leaflets may be constructed of expanded polytetrafluoroethylene (ePTFE), equine pericardium, bovine pericardium, or native porcine valve leaflets similar to currently available bioprosthetic aortic valves. Other materials may prove suitable as will be appreciated by one skilled in the art.

As indicated above, one or more embodiments of the prosthetic valves described herein achieve one or more of the following objectives: (1) durability the same or better than convention replacement valves; (2) valve in valve suitability; (3) hemodynamics the same or better than conventional valves; (4) reproducible minimally invasive procedure; (5) ease of implant; (6) first time deployment accuracy; and (7) reduced cardiopulmonary bypass (CPB) and cross clamp times; (8) reduced complications and improved safety; and (9) improved implantability. In some embodiments, a prosthetic valve described herein has one or more of the following features: (1) frame height suitable to accommodate aortotomy two centimeters above STJ maximum height, while being as short as possible; (2) avoidance of crown-like structure/rail in outflow; (3) maintain access to coronaries; (4) active fixation in inflow as part of frame; (5) frame depth preferably does not sit lower than four to six millimeters below annulus; and (6) stabilization feature. In some embodiments, prosthetic valves disclosed herein incorporate one or more of the following design considerations: (1) supra-annular attachment of valve in frame; (2) scalloped inflow; (3) bovine, porcine or equine pericardium; and (4) minimize crimping impact on valve tissue.

While not every prosthetic valve system described herein meets every objective, feature or design consideration outlined above, the valve frames and systems described below with preferably achieve one or more of the objectives, features or design consideration outlined above.

Figure 6:
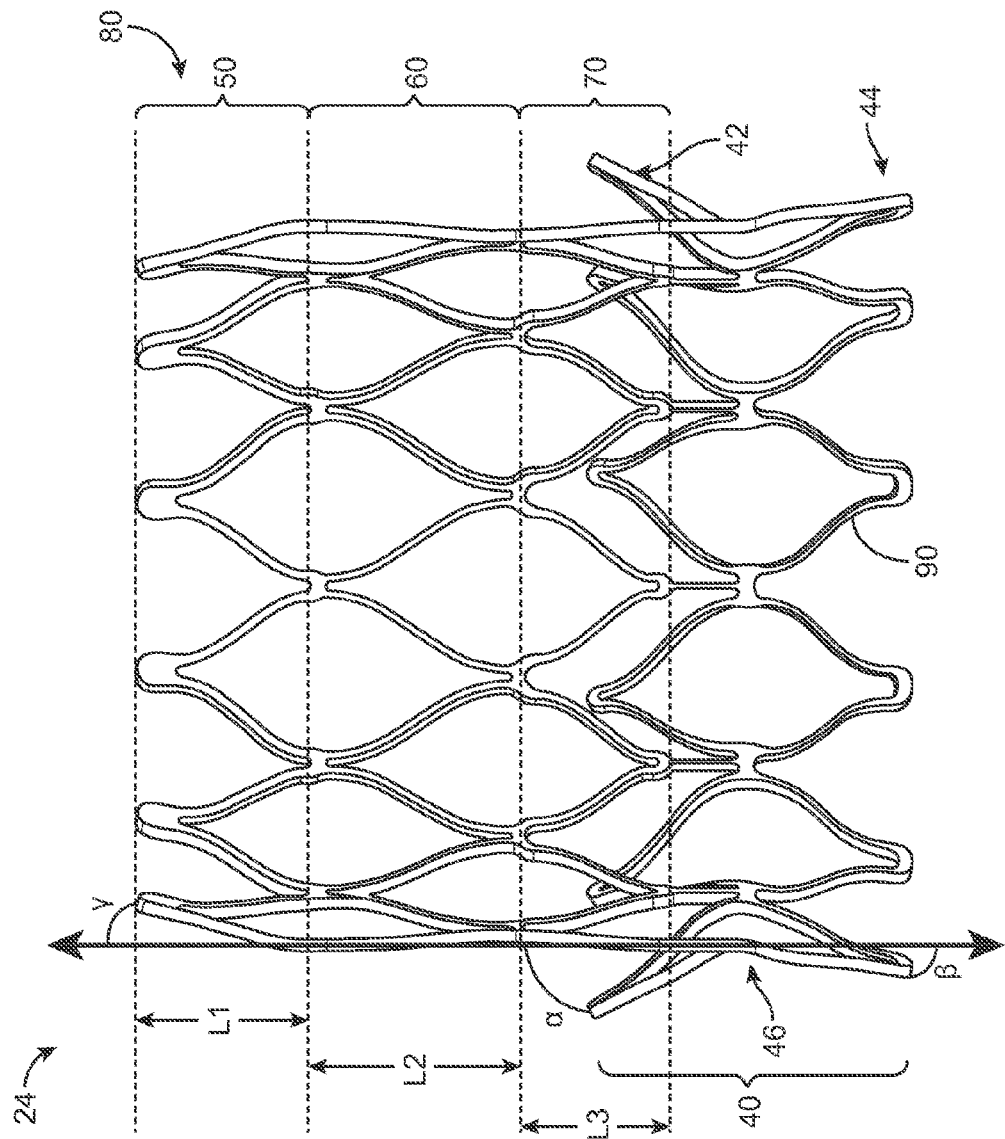
FIGS. 6-7 are schematic sectional plan views of roughly half of an embodiment of a prosthetic valve frame.
Figure 7:
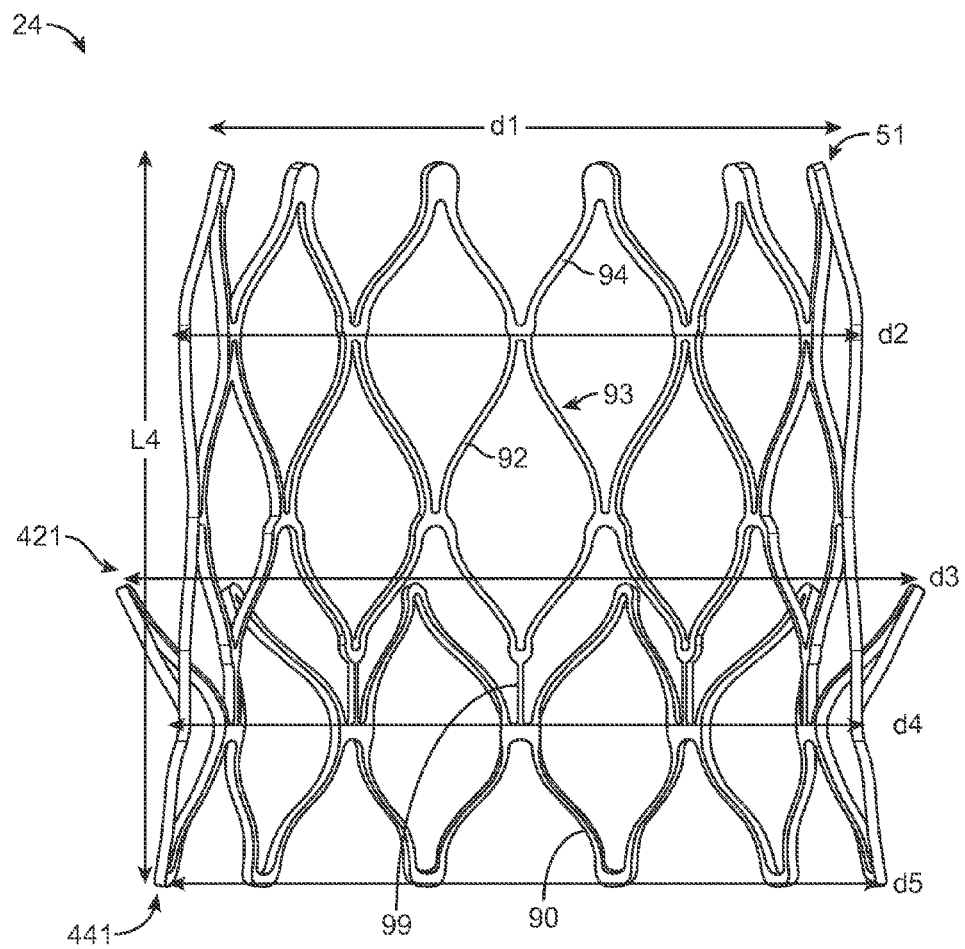
Figure 8:
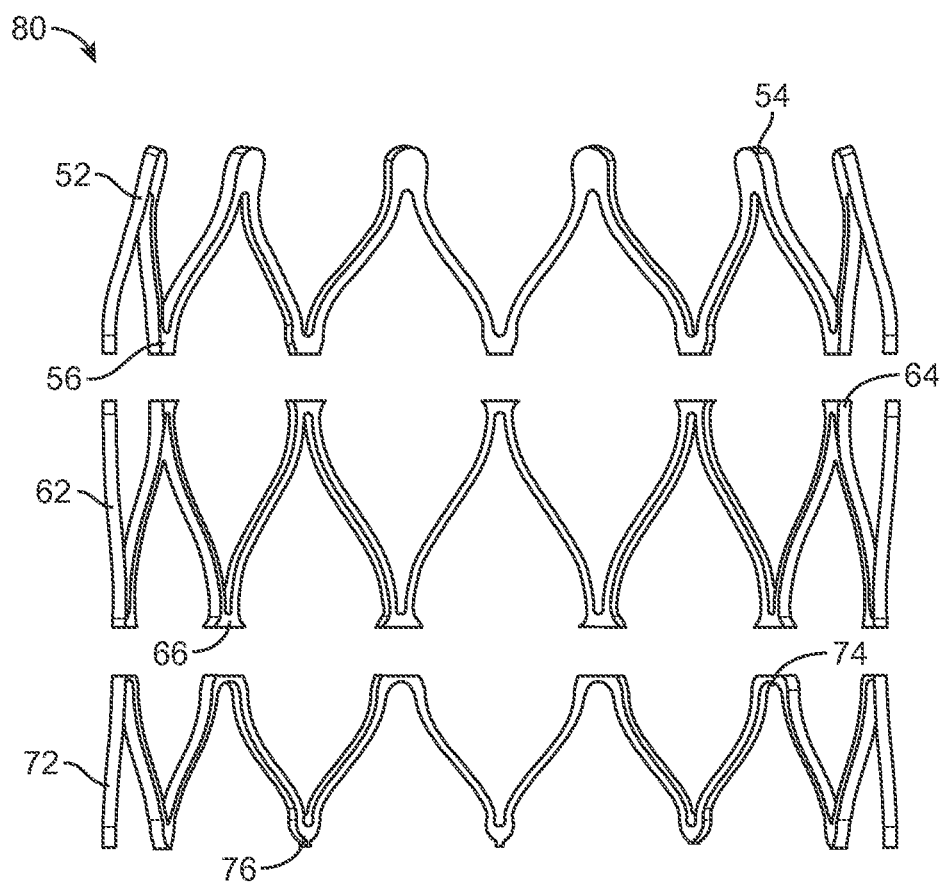
FIG. 8 is schematic view of the outflow portion of the frame depicted in FIGS. 6-7, in which portions are depicted as being separated.
Figure 9:
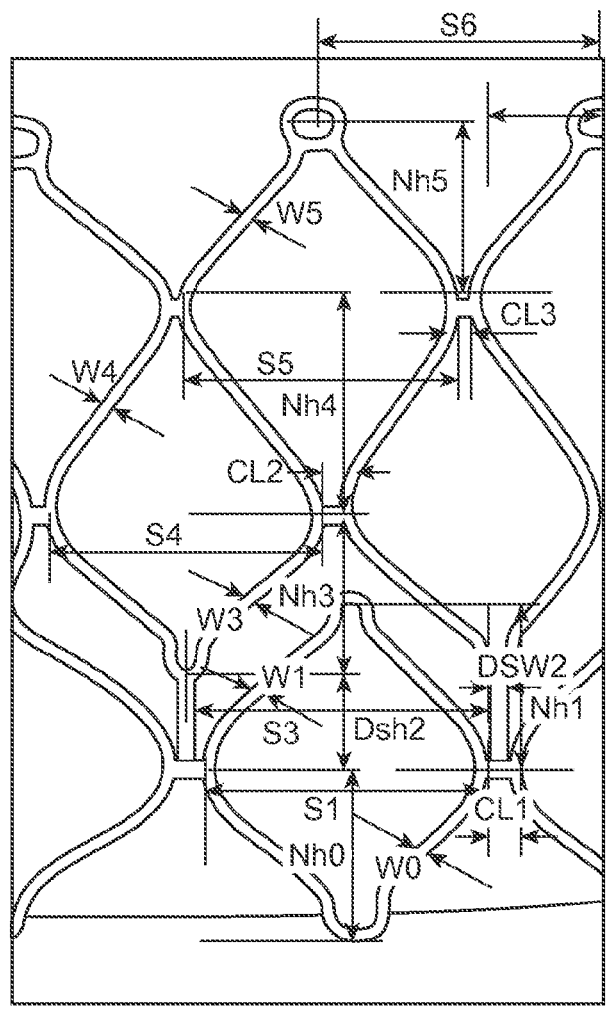
FIG. 9 is schematic drawing of a frame according to an embodiment described herein.

Referring now to FIGS. 6-9, similar embodiments of an expandable prosthetic valve frame 24 is depicted. In FIGS. 6-7 a sectional plan view showing roughly half of an embodiment of a frame 24 in a fully expanded configuration is depicted. FIG. 8 shows a sectioned outflow portion of the frame depicted in FIGS. 6-7, in which the depicted sections are separated along the transition from (i) the upper outflow portion 50 and the middle outflow portion 60, and (ii) the middle outflow portion 60 and the lower outflow portion 70. FIG. 9 is an schematic drawing of a portion of an embodiment of a frame.

The frame 24 depicted in FIGS. 6-9 has an outflow portion 80 and an inflow portion 40 connected to the outflow portion 80. The frame 24 defines a central lumen extending between the outflow portion and the inflow portion. The frame is generally cylindrical in its fully expanded configuration (i.e., a configuration in which the frame is expanded no external forces are applied to the frame). The frame 24 is configured to receive a valve body in the central lumen. The valve body (not shown in FIGS. 6-9) may be affixed to the frame.

As depicted in FIGS. 6-9, when the frame 24 is in the fully expanded configuration, an outer surface of the inflow portion 40 is concave. The inflow portion 40 has an upper inflow portion 42 and a lower inflow portion 44 and a waist 46 between the upper and lower inflow portions. As depicted, the upper inflow portion flares outwardly from the central lumen of the frame to greater extent than the lower inflow portion. Without intending to be bound by theory, it is believed that better anchoring (relative to configurations where the upper inflow portion and the lower inflow portion flare to the same extent) with the inflow annulus of a native valve, such as a native heart valve, or improved implantation can be achieved from such configurations.

In various embodiments, the upper inflow portion 42 flares outwardly from the longitudinal axis of the frame at an angle $\alpha$ that is greater than an angle $\beta$ at which the lower inflow portion 44 flares. In some embodiments, the upper inflow portion flares outwardly away from the longitudinal axis of the frame at an angle from about 40° to about 60°, such as from about 45° to about 55°, or about 50°. In some embodiments, the lower inflow portion flares from the longitudinal axis of the frame at an angle from about 10° to about 30°, such as from about 15° to about 25°, or about 20°.

Still referring to FIGS. 6-9, the upper inflow portion 42 defines an edge 421 having a circumference, and the lower inflow portion 44 defines an edge 441 having a circumference. The diameter d3 of the upper inflow portion edge 421 is greater than the diameter d5 of the lower inflow portion edge 441. In some embodiments, the diameter of the upper inflow edge is from about 115% to about 135%, such as from about 120% to about 130% or about 125% of the diameter d4 of the inflow waist 46. In some embodiments, the diameter of the lower inflow edge is from about 105% to about 120%, such as about 108% to about 117%, or about 112% of the diameter of the waist. In some embodiments, the diameter of the upper inflow edge is from about 105% to about 115%, or about 110% of the diameter of the lower inflow edge.

In some embodiments, the diameter d4 of the inflow waist 46 is from about 24 mm to about 27 mm, such as from about 25 mm to about 26 mm, or about 25.5 mm. In some embodiments, the diameter d3 of the upper inflow portion edge 421 is from about 30 mm to about 33 mm, such as from about 31 mm to about 32 mm, or about 31.5 mm. In some embodiments, the diameter d5 of the lower inflow portion edge 441 is from about 27 mm to about 30 mm, such as from about 28 mm to about 29 mm, or about 28.5 mm.

As shown in FIGS. 6-9, the inflow portion 40 of the frame 24 comprises a plurality of closed cells 90, where each cell is connected to an adjacent cell along the waist 46.

An inflow portion 40 of a frame as depicted in FIG. 6-9 may be connected to any suitable outflow portion. In the embodiments depicted in FIGS. 6-9, the outflow portion 80 of the frame 24 has an upper portion 50 flared inwardly towards the central lumen. In the depicted embodiments, the lower outflow portion 70 and a middle outflow portion 60 are together are generally cylindrical, the upper outflow portion 50 defines an edge 51 defining a circumference, and the diameter d1 of the edge of the upper outflow portion is from about 75% to about 97%, such as from about 80% to about 95%, or about 87% of the diameter d2 of the middle and lower outflow portions.

In some embodiments, the diameter d1 of the edge of the upper outflow portion is from about 21 mm to about 25 mm, such as from about 22 mm to about 23 mm, or about 22.5 mm. In some embodiments, the diameter d2 of the middle and lower outflow portions is from about 24 mm to about 27 mm, such as about 25 mm to about 26 mm, or about 25.5 mm.

The outflow portion 80 has an undulating upper section 52 having peaks 54 and valleys 56, an undulating middle section 62 having peaks 54 and valleys 56, and an undulating lower section 72 having peaks 74 and valleys 76. The undulating section may be have a repeating pattern as depicted in FIGS. 6-9 but may be irregular. The valleys 56 of the undulating upper section 52 are connected to the peaks 64 of the undulating middle section 62, thereby forming upper closed cells 94 extending the length of the middle 60 and upper outflow 50 portions. The adjacent cells are connected at the intersection of the middle 60 and upper 50 outflow portions. The valleys 66 of the undulating middle section 62 are connected to the peaks 74 of the undulating lower section 74, thereby forming lower closed cells 92 extending the length of the lower 70 and middle 60 outflow portions Adjacent cells 92 are coupled at the intersection of the lower 70 and middle 60 outflow portions. Adjacent upper 94 and middle 92 closed cells share a side 93 in the middle outflow portion 60.

In embodiments (e.g., as depicted in FIGS. 6-7 and 9), one or more of the valleys 76 of the undulating lower section 72 are connected to the inflow portion 40 along the waist 46 between closed cells 90. The valleys 76 of the undulating lower section 72 may be connected to the inflow portion 40 via one or more posts 99.

The upper outflow portion 50, the middle outflow portion 60 and the lower outflow portion 70 may have any suitable height. In some embodiments, the length L1 of the upper outflow portion 50 is greater than the length L3 of the lower outflow portion 70, and the length of the upper outflow portion 50 is less than the length L2 of the middle outflow portion 60.

In embodiments, the frame 24 has a height L4 of from about 25 mm to about 29 mm, such as from about 26 mm to about 28 mm, or about 27 mm.

As depicted in FIGS. 6-9, a frame 24 may comprise a plurality of enclosed wire form cells interconnected with one another. In embodiments, the frame has from 9 to 15 cells, such as 12 cells, formed around a circumference of the frame. The wall of the frame may have any suitable thickness, such as from about 0.3 mm to about 0.6 mm, or about 0.45 mm. The width of the wire frame at various locations may vary. By varying the width of the frame along the length or at various sections, the frame may expand in a desired or predictable manner.

Referring now to FIG. 9, the various dimensions are depicted. Such dimensions may have any suitable size. In embodiments, the dimensions depicted in FIG. 9 are within the ranges of sizes or are the sizes presented below in Table 1.

TABLE 1

Examples of various dimensions of frame (with reference to FIG. 9)

| Dimension Identifier | Example Size Range (mm) | Example Size (mm) |
| --- | --- | --- |
| Nh0 | 3.9-4.9 | 4.4 |
| Nh1 | 5.0-7.0 | 6.0 |
| Nh3 | 4.8-5.8 | 5.33 |
| Nh4 | 6.4-7.4 | 6.9 |
| Nh5 | 5.15-6.15 | 5.65 |
| W0 | 0.15-0.25 | 0.25 |
| W1 | 0.30-0.50 | 0.40 |
| W3 | 0.22-0.34 | 0.29 |
| W4 | 0.16-0.26 | 0.21 |
| W5 | 0.29-0.43 | 0.38 |
| S1 | 5.0-5.7 | 5.5 |
| S3 | 6.1-6.5 | 6.4 |
| S4 | 5.4-6..0 | 5.8 |
| S5 | 5.8-6.2 | 6.1 |
| S6 | 6.5-6.8 | 6.7 |
| CL1 | 1.0-1.5 | 1.22 |
| CL2 | 0.65-1.15 | 0.90 |
| CL3 | 0.45-0.70 | 0.57 |
| DSh2 | 2.0-4.0 | 2.75 |
| DSW2 | 0.2-0.42 | 0.32 |

Figure 10:
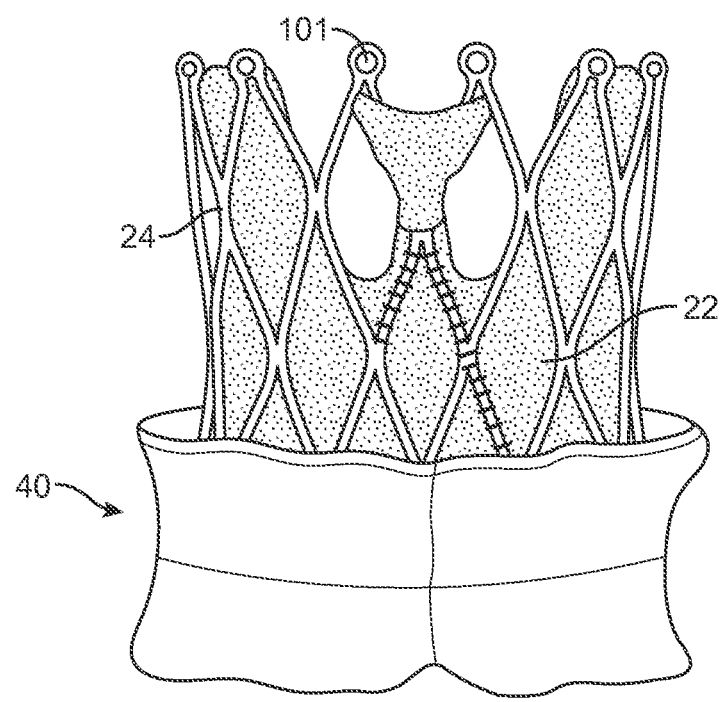

Referring now to FIG. 10, an embodiment of a prosthetic replacement valve device is shown. The depicted device has a concave inflow portion 40 similar to the inflow portion depicted in and described above with regard to FIGS. 6-9. A skirt 60 is disposed about the inflow region 40. The skirt 60 has markings around the circumference of the waist of the inflow for alignment with an inflow annulus of a native valve and along the length of the skirt to identify replacement valve commissures and for aligning with native valve commissures during implant.

Any prosthetic valve device described herein may have a skirt, which may have one or more markings. The markings may be as described in, for example, (i) U.S. Provisional Patent Application No. 61/930,851, filed on Jan. 23, 2014, (ii) U.S. Provisional Patent Application No. 61/819,486 filed on May 3, 2013 (to which the present application claims priority), or (iii) U.S. patent application Ser. No. 14/268,393, filed on the same day as the present application, entitled MEDICAL DEVICES FOR IMPLANTING IN A VALVE AND ASSOCIATED METHODS, and having attorney docket no.

C00007020.USU2, each of which is hereby incorporated herein by reference in their respective entireties to the extent that they do not conflict with the disclosure presented herein.

Referring again to FIG. 10, the depicted device includes replacement valve 22 affixed to frame 24. In the depicted device, the valve is attached to the frame 24 via sutures.

A replacement valve may be attached to a frame described herein in any suitable location and via any suitable mechanism.

The device depicted in FIG. 10 includes eyelets 101 at the upper outflow portion. The eyelets 101 may be used for connecting the device to a valve delivery device. Any prosthetic valve device described herein may include one or more eyelets or other suitable features for engaging a valve delivery system.

Figure 11A:
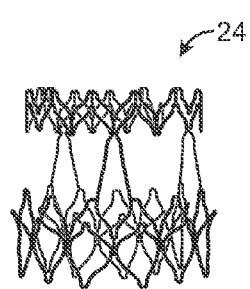
Figure 11B:
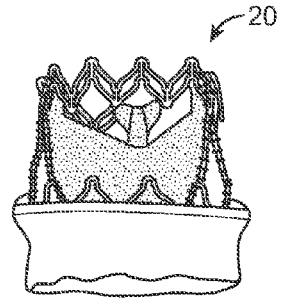
Figure 11C:
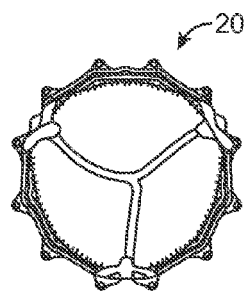
Figure 11D:
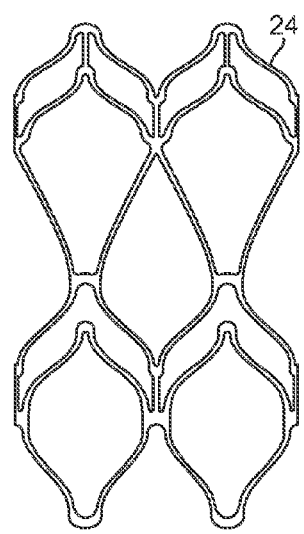
Figure 11E:
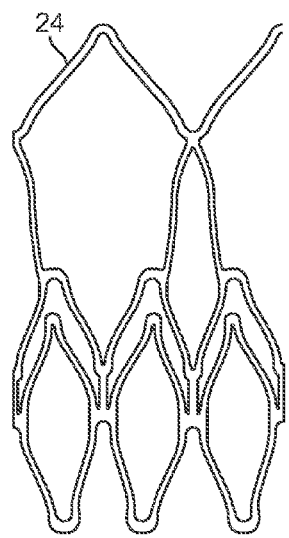

Referring now to FIGS. 11A-E, embodiments of replacement heart valve systems 20 and corresponding frames 24 are shown. In FIG. 11A only the frame 24 is shown. As can be seen, the inflow rim (the bottom) of the frame has concave elements, that when expanded, are configured to engage the annulus (or configured to cause a skirt to engage the annulus) of a native valve to prevent PVL. The concave inflow region may be a region as described above with regard to FIGS. 6-9 or may be a concave landing area as described in, for example, US Published Patent Application No. 2010/0100176. FIG. 11B shows the valve and valve cuff connected to the frame, and FIG. 11C is a top-down view. The valve is connected to the frame above closed cells that connect the outflow rim (top of FIG. 11A) to the inflow rail. The closed cells improve crimpability (uniformity and consistency) relative to frames with support posts, such as described in US 2012/0165544. FIG. 11D shows a 12/12 closed-cell design. FIG. 11E shows a 18/9 converging closed cell design.

Figure 12A:
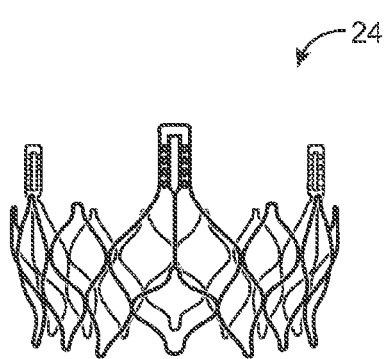
Figure 12B:
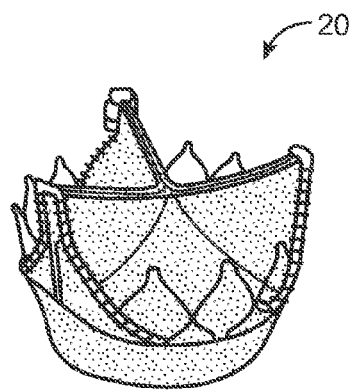
Figure 12C:
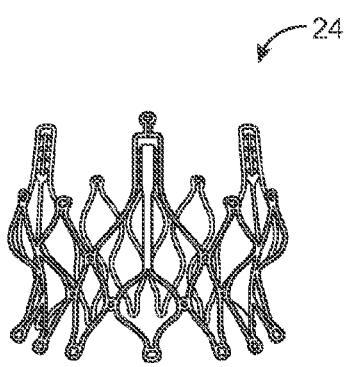
Figure 12D:
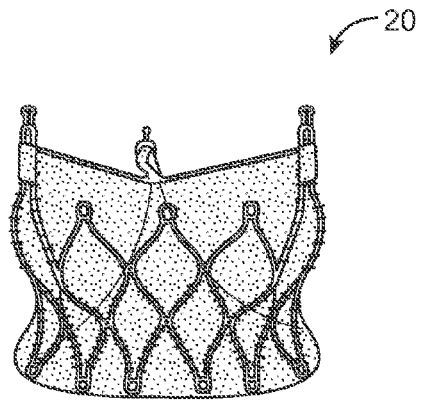
Figure 15A:
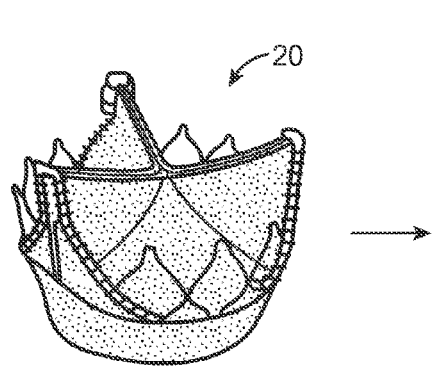
Figure 15B:
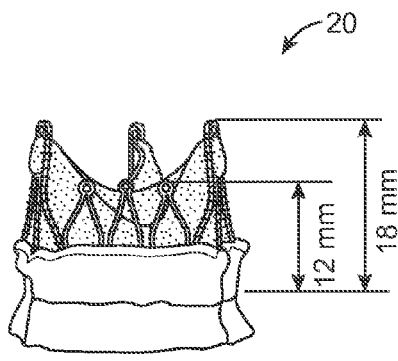
Figure 16A:
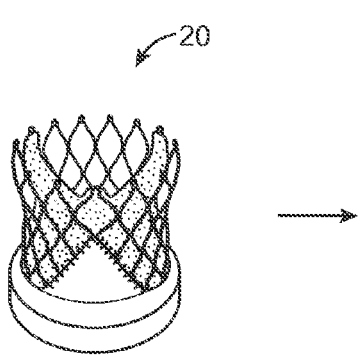
Figure 16B:
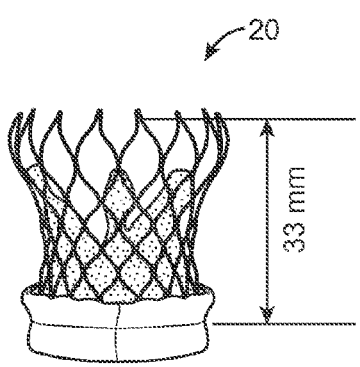

Referring now to FIGS. 12A-D, embodiments of replacement heart valve systems 20 and corresponding frames 24 are shown. FIG. 12A shows a frame only, and FIG. 12B shows the corresponding frame with attached valve. FIG. 12C shows another embodiment of a frame only, and FIG. 12D shows the corresponding frame with attached valve. The frames in FIGS. 12A-D are of a lower profile than those depicted in FIGS. 11A-D. This is accomplished by the lack of an intervening frame section or structure connecting the inflow rail to the outflow rail. As with the designs shown in FIGS. 11A-D, the designs shown in FIGS. 12A-D include a concave landing zone at the inflow rail for active fixation to the native valve annulus such as an aortic valve annulus, when expanded. The designs shown in FIGS. 12A-D have a contoured frame body, an outflow region designed to stabilize the frame in the native valve, and may have stiffer frames to maintain circularity in an elliptical annulus. Differences in the designs between FIGS. 12A and 12B and FIGS. 12C and 12D include elongated cells (in 12C and 12D) to achieve a more flared profile (inflow cells deeper and more flared inward to mitigate perforation) and a taller valve skirt to promote seal.

Referring now to FIGS. 13A-C, the evolution of a design of an embodiment of a replacement heart valve system is shown. FIG. 13A shows a Medtronic, Inc. CoreValve® valve that has been implanted in thousands of patients and has cells that allow passage of an 8F catheter for coronary interventions. However, the valve system shown in FIG. 13A may be too tall for surgical application. As shown in FIG. 13B, the valve attachment region of FIG. 13A is preserved, while ends of the frame that do not directly impact valve design were removed. The valve system in FIG. 13C includes an active fixation inflow end that in hung from the frame of FIG. 13B.

FIGS. 14A-B, 15A-B, and 16A-B also show evolutions of designs. The design change from FIG. 14A to FIG. 14B includes a closed cell structure to stabilize frame crimping and commissure post deflection. The design change from FIG. 15A to FIG. 15B includes modification of the frame profile to reduce radial interference. The design change from FIG. 16A to FIG. 16B includes replacing double flange inflow design with flared inflow collar design to provide active fixation and added outflow cells to improve valve coaptation. Various profile heights are also depicted in FIGS. 14A-B, 15A-B, and 16A-B. It will be understood that the replacement valve systems and associated frames may have any suitable height and that the heights depicted in FIGS. 14A-B, 15A-B, and 16A-B are shown for purposes of example.

Figure 17:
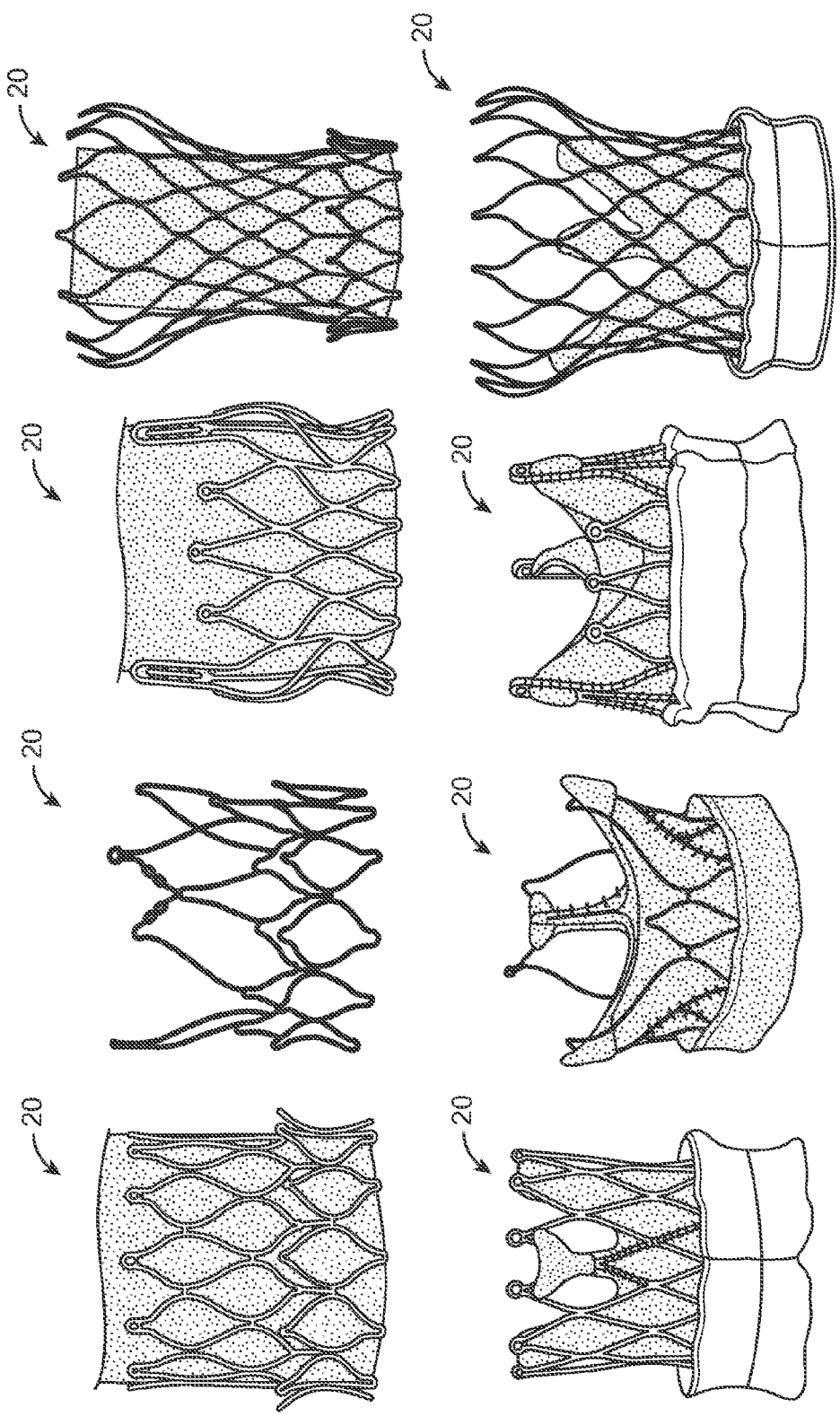

FIG. 17 shows a summary of some of the various device 20 designs described above and illustrates some distinguishing features.

Figure 18:
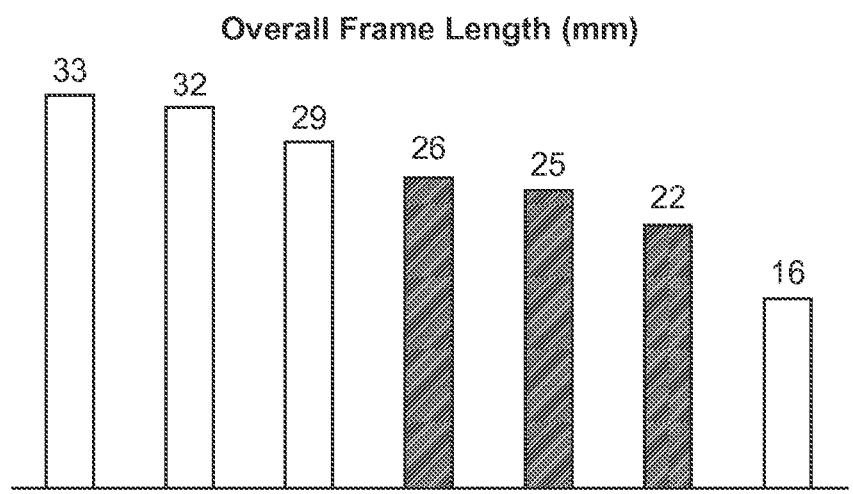
FIG. 18 is a graph of overall length of various prototype frames described herein.
Figure 19:
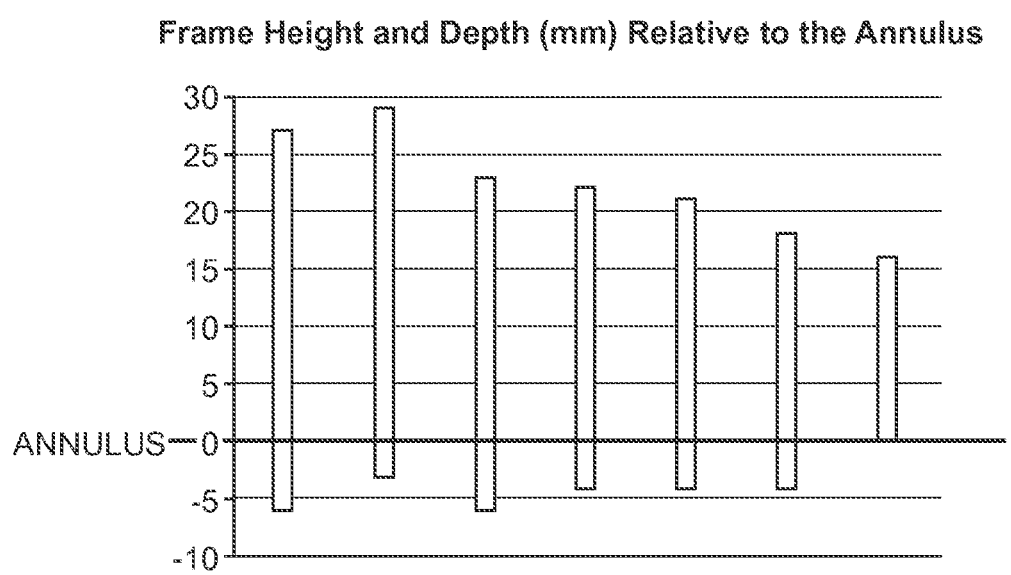
FIG. 19 is a graph of height and depth of various prototype frames described herein.

FIGS. 18 and 19 are graphs showing overall frame length (18) and frame height and depth relative to the annulus (19) of various designs, including some previously developed designs for purposes of comparison.

Figure 20:
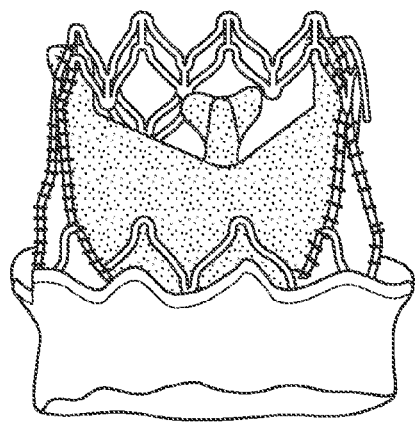
Figure 21:
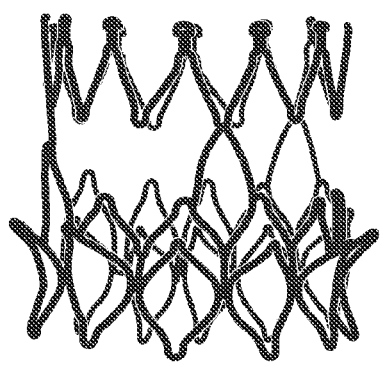
Figure 22:
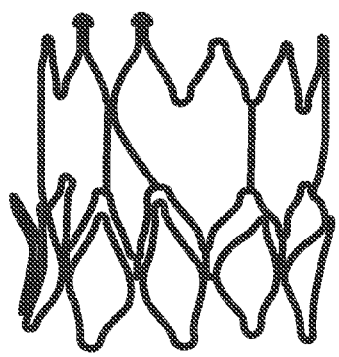

Various designs of replacement valve systems will now be discussed with reference to FIGS. 20-38. Some of the designs may be the same or similar to those discussed above. Referring now to FIGS. 20-22, an open cell designs are shown. The designs have an hourglass shape that allows self-aligning to the aortic valve annulus and are resistant to migration due to the upper flare. The collar is nested underneath the rail and moves valve attachment within the frame to supra-annular position to limit valve deformation if native valve annulus is not round. The designs include a strut-based commissure post design rather than a solid post. This avoids abrupt stiffness transitions at the outflow rail to improve fatigue performance. Eyelets are on the outflow rail for delivery tool attachment.

Figure 23:
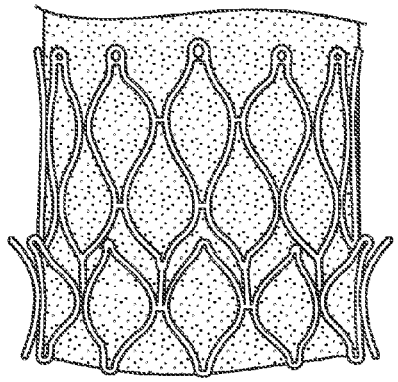
Figure 24:
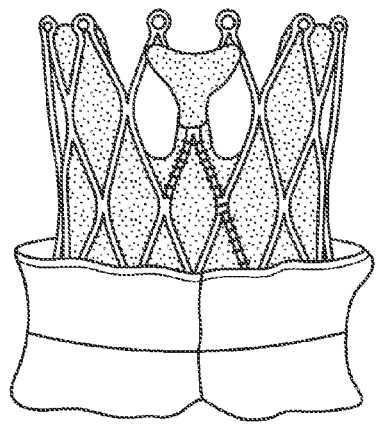

Referring now to FIGS. 23-24, closed cell designs are shown. Like designs shown in FIGS. 20-22, the designs shown in FIGS. 23-24 include an inflow collar configured to actively fix to the native valve annulus (when expanded), collar nested underneath the rail, and eyelets on outflow rail for delivery tool attachment. The designs shown in FIGS. 23-24 also include closed cell geometry for more uniform crimping and structural redundancy (relative to open cell geometry). Uniform crimping prevents misalignments that can elevate crimp strains and reduce fatigue life. An indicator line is also provided in the skirt, as shown in FIG. 24, to provide a visual target for alignment of the waist to the native valve annulus. Vertical indicator lines indicate commissure post locations as visual targets for valve orientation.

Figure 25:
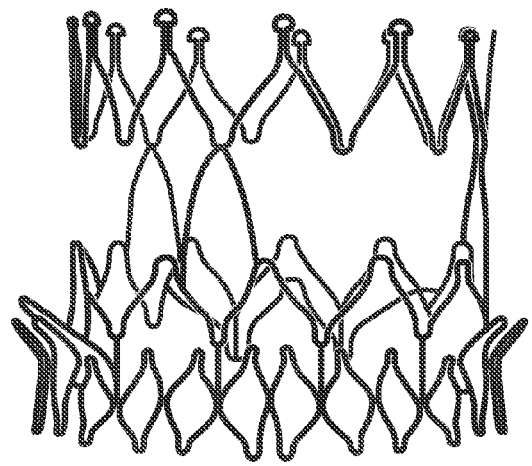

Referring now to FIG. 25, an unbalanced inflor collar design is shown. As with the designs of FIGS. 23-24, the design of FIG. 25 includes an inflow collar configured to actively fix to the native valve annulus (when expanded), collar cells nested underneath the rail, and eyelets on outflow rail for attachment of a delivery tool. Due to the unbalanced inflow collar design, a larger number of cells in the lower portion of the collar converge into fewer cells in the upper portion. This provides a way to minimize implant depth below the annulus, while preserving collar overhang above the annulus. The open-cell design inflow collar makes the collar more conformable, potentially reducing PVL.

Referring now to FIGS. 26A-B, 27A-B and 28A-B, converging cell designs are shown. FIGS. 26A, 27A and 28A depict only a frames, while FIGS. 26B, 27B and 28B depict the corresponding frames and attached valves. As with the designs of FIGS. 20-25, the design of FIGS. 26A-B, 27A-B and 28A-B include an inflow collar configured to actively fix to the native valve annulus (when expanded), collar cells nested underneath the rail, and eyelets for attachment of a delivery tool. The converging cell geometry of FIGS. 26A-B, 27A-B and 28A-B results in inflow cell merged in commissure design to yield three distinct commissure posts with no outflow rail connecting them. The absence of an outflow rail may improve visualization of valve position in relation to aortic root anatomy after deployment. The outflow portion of the frame in FIGS. 26A-B, 27A-B and 28A-B tapers outward and reduces commissure deflection under closing pressures.

Figure 29:
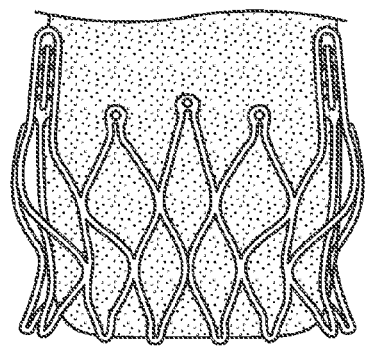
Figure 30:
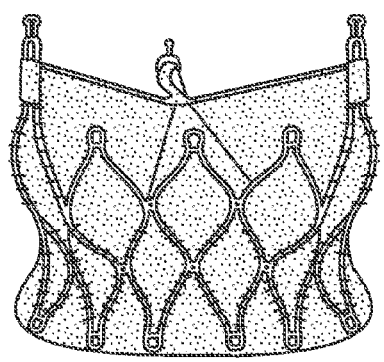
Figure 31:
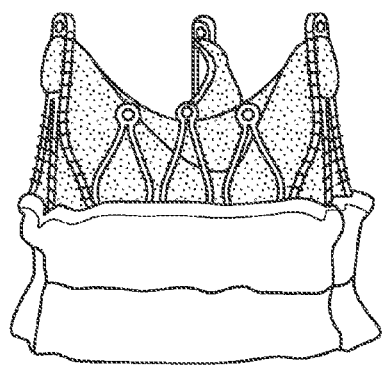

Referring now to FIGS. 29-31, flared-body designs are shown. As with some of the previously described designs, the designs shown in FIGS. 29-31 include eyelets for attachment of a delivery tool, indicator lines on the skirt, and distinct commissure posts. The flared-body design allows for active fixation to the native valve annulus (when expanded) within the core of the frame rather than using a separate row of cells. This can provide for a lower profile. In the designs shown in FIGS. 29-31 the frame bulges out above the annulus, allowing for engagement with the native valve annulus to provide stability against tilting or migration.

Figure 32:
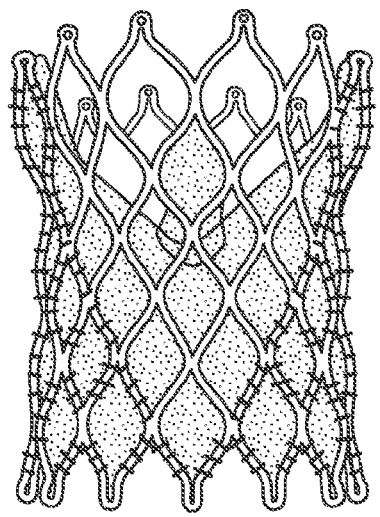
Figure 33:
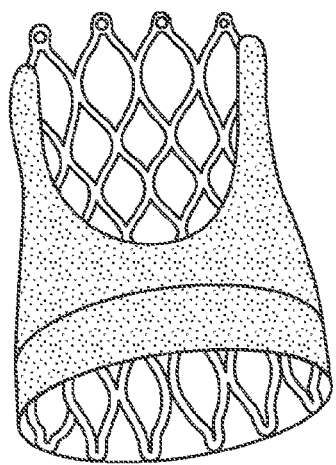
Figure 34:
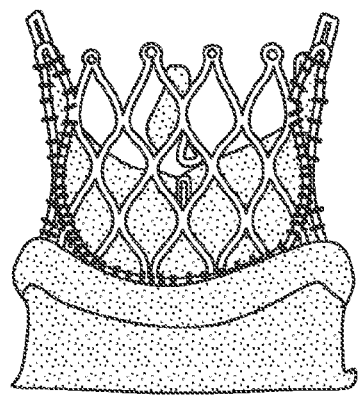

Referring now to FIGS. 32-34, shortended CoreValve-like designs are shown. As with some of the previously described designs, the designs shown in FIGS. 32-34 include closed cell geometry and indicator lines on the skirt. The designs shown in FIGS. 32-34 include a single sewing cuff, which may be straight or scalloped, to promote a seal. A double flange serving cuff may be used to promote a seal. Such a cuff design is described in more detail in, for example, US 2010/0168844.

Figure 35:
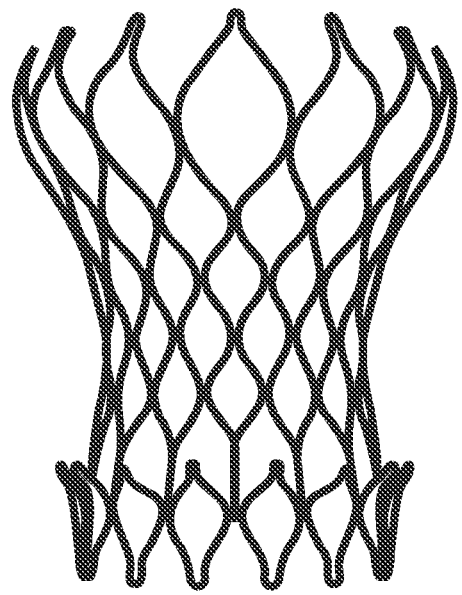
Figure 36:
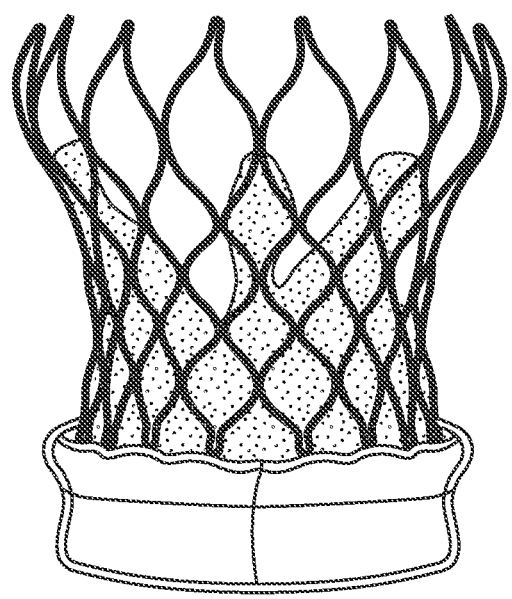

Referring now to FIGS. 35-36, CoreValve-like designs with an inflow collar are shown. The designs are similar to those depicted in FIGS. 23-34, but include an active fixation (when expanded) inflow collar.

The prosthetic valve systems described herein may be implanted in any suitable manner. For example, implant methods, valve delivery systems and associated devices that may be employed with the replacement valve systems described herein are disclosed in U.S. patent application Ser. No. 14/268,375, entitled VALVE DELIVERY TOOL, having attorney docket no. C00001363.USU2, filed on the same day as the present application, which application is hereby incorporated herein by reference in its entirety to the extent that it does not conflict with the present disclosure.

A number of embodiments of valve prostheses and frames for valve prostheses are described herein. A summary of a few select aspects is provided below.

In a first aspect, a valve prosthesis comprises an expandable frame comprising an outflow portion and an inflow portion connected to the outflow portion. The frame defines a central lumen extending between the outflow portion and the inflow portion. The frame is generally cylindrical in a fully expanded configuration. When the frame is in the fully expanded configuration, an outer surface of the inflow portion is concave. The inflow portion has an upper inflow portion and a lower inflow portion. When the frame is in the fully expanded configuration, the upper inflow portion flares outwardly from the central lumen of the frame to greater extent than the lower inflow portion.

A $2^{nd}$ aspect is a valve prosthesis according to the $1^{st}$ aspect, wherein the inflow portion of the frame further comprises a waist between the upper inflow portion and lower inflow portion, wherein the frame in the fully expanded configuration has a longitudinal axis, wherein the upper inflow portion flares outwardly away from the longitudinal axis at an angle that is greater than an angle at which the lower inflow portion flares.

A $3^{rd}$ aspect is a valve prosthesis according to the $2^{nd}$ aspect, wherein the upper inflow portion flares outwardly from the longitudinal axis of the frame at an angle from about 40° to about 60°, and wherein the lower inflow portion flares outwardly from the longitudinal axis of the frame at an angle from about 10° to about 30°.

A fourth aspect is a valve prosthesis according to the second aspect, wherein the upper inflow portion flares outwardly from the longitudinal axis of the frame at an angle from about 45° to about 55°, and wherein the lower inflow portion flares outwardly from the longitudinal axis of the frame at an angle from about 15° to about 25°.

A $5^{th}$ aspect is a valve prosthesis according to any of the preceding aspects, wherein the inflow portion of the frame further comprises a waist between the upper inflow portion and lower inflow portion, wherein the upper outflow portion forms an upper outflow edge defining a circumference and the lower outflow portion forms a lower edge defining a circumference, wherein the diameter of the upper inflow edge is from about 115% to about 135% of a diameter of the inflow waist and wherein the diameter of the lower inflow edge is from about 105% to about 120% of the diameter of the waist, provided that the diameter of the upper inflow edge is greater than the diameter of the lower inflow edge.

A $6^{th}$ aspect is a valve prosthesis according to the $5^{th}$ aspect, wherein the upper inflow edge is from about 120% to about 130% of the diameter of the inflow waist and wherein the diameter of the lower inflow edge is from about 108% to about 117% of the diameter of the waist, provided that the diameter of the upper inflow edge is greater than the diameter of the lower inflow edge.

A $7^{th}$ aspect is a valve prosthesis according to any one of the preceding aspects, wherein the upper outflow portion of the frame forms an upper outflow edge defining a circumference and the lower outflow portion forms a lower edge defining a circumference, wherein the diameter of the upper inflow edge is from about 105% to about 115% of the diameter of the lower inflow edge.

An $8^{th}$ aspect is a valve prosthesis according to any one of the preceding aspects, wherein the inflow portion of the frame comprises a waist between the lower inflow portion and the upper inflow portion, and wherein the inflow region comprises a plurality of closed cells, wherein each cell is connected to an adjacent cell along the waist.

A $9^{th}$ aspect is a valve prosthesis according to any one of the preceding aspects, wherein the outflow portion of the frame has an upper portion flared inwardly towards the central lumen.

A $10^{th}$ aspect is a valve prosthesis according to the $9^{th}$ aspect, wherein the outflow portion of the frame has a lower portion and a middle portion that together are generally cylindrical, wherein the upper outflow portion defines an edge defining a circumference, and wherein the diameter of the edge of the upper outflow portion is from about 75% to about 97% of the diameter of the middle and lower outflow portions.

An $11^{th}$ aspect is a valve prosthesis according to the $10^{th}$ aspect, wherein the diameter of the edge of the upper outflow portion is from about 80% to about 95% of the diameter of the middle and lower outflow portions.

A $12^{th}$ aspect is a valve prosthesis according to any one of the preceding aspects, wherein the outflow portion comprises (i) an undulating upper outflow portion having peaks and valleys, (ii) an undulating middle outflow portion having peaks and valleys, and (iii) an undulating lower outflow portion having peaks and valleys, wherein the valleys of the undulating upper outflow portion are connected to the peaks of the undulating middle inflow portion, and wherein the valleys of the undulating middle outflow portion are connected to the peaks of the undulating lower outflow portion.

A 13th aspect is a valve prosthesis according to the 12th aspect, wherein the height of the upper outflow portion is greater than the height of the lower outflow portion, and wherein the height of the upper outflow portion is less than the height of the middle outflow portion.

A 14th aspect is a valve prosthesis according to the 12th aspect or the 13th aspect, wherein the inflow portion has a waist between the lower inflow portion and the upper inflow portion, wherein the lower inflow portion comprises a plurality of closed cells connected along the waist, and wherein the valleys of the undulating lower outflow portion are connected to the inflow portion along the waist between the closed cells.

A 15th aspect is a valve prosthesis according to the 14th aspect, wherein the valleys of the undulating lower outflow portion are connected to the inflow portion along the waist via posts.

A 16th aspect is a valve prosthesis according to any one of the preceding aspects, wherein the frame comprises a plurality of enclosed wire form cells interconnected with one another.

A 17th aspect is a valve prosthesis according to any one of the preceding aspects, wherein the frame is a self-expanding frame.

An 18th aspect is a valve prosthesis according to any one of the preceding aspects, further comprising a valve body comprising a plurality of leaflets affixed to a skirt, wherein adjoining leaflets are affixed together to form commissures, and wherein the valve body is disposed in the central lumen of the frame and the commissures are affixed to the outflow portion.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, article, system, method or the like, means that the components of the composition, article, system, method or the like are limited to the enumerated components and any other components that do not materially affect the basic and novel characteristic(s) of the composition, article, system, method or the like.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, the term "about" encompasses the range of experimental error that occurs in any measurement or manufacturing tolerances that may result in variances.

As used herein, "exemplary" means serving as an example and does not necessarily imply that the example is preferable or the best of its kind.

Spatially related terms, including but not limited to, "top", bottom", "front", "rear", "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

INCORPORATION BY REFERENCE

Any patent or non-patent literature cited herein is hereby incorporated herein by reference in its entirety to the extent that it does not conflict with the disclosure presented herein.

In the detailed description above several specific embodiments of compounds, compositions, articles, systems and methods are disclosed. It is to be understood that other embodiments are contemplated and may be made without departing from the scope or spirit of the present disclosure. The detailed description, therefore, is not to be taken in a limiting sense.

Thus, embodiments of PROSTHETIC VALVES AND ASSOCIATED APPARATUSES, SYSTEMS AND METHODS are disclosed. One skilled in the art will appreciate that the heart valves and associated apparatuses, systems and methods described herein can be practiced with embodiments other than those disclosed. The disclosed embodiments are presented for purposes of illustration and not limitation.

What is claimed is:

1. A valve prosthesis comprising:
an expandable frame comprising an outflow portion and an inflow portion connected to the outflow portion, the frame defining a central lumen extending between the outflow portion and the inflow portion, wherein the frame is generally cylindrical in a fully expanded configuration,
wherein, when the frame is in a fully expanded configuration, an outer surface of the inflow portion is concave, wherein the inflow portion has an upper inflow portion and a lower inflow portion, and wherein, when the frame is in the fully expanded configuration, the upper inflow portion flares outwardly from the central lumen of the frame to greater extent than the lower inflow portion,
wherein the outflow portion comprises (i) an undulating upper outflow portion having peaks and valleys, (ii) an undulating middle outflow portion having peaks and valleys, and (iii) an undulating lower outflow portion having peaks and valleys, wherein the valleys of the undulating upper outflow portion are connected to the peaks of the undulating middle inflow portion, and wherein the valleys of the undulating middle outflow portion are connected to the peaks of the undulating lower outflow portion; and
wherein a height of the upper outflow portion is greater than a height of the lower outflow portion, and wherein the height of the upper outflow portion is less than a height of the middle outflow portion.

2. A valve prosthesis according to claim 1, wherein the upper inflow portion defines an upper inflow edge and wherein the lower inflow portion defines a lower inflow edge, and wherein the lower inflow edge flares outwardly from the central lumen and from the longitudinal axis of the frame.

3. A valve prosthesis according to claim 2, wherein the inflow portion of the frame further comprises a waist between the upper inflow portion and the lower inflow portion, wherein the upper inflow edge defining a circumference and the lower inflow edge defining a circumference, wherein a diameter of the upper inflow edge is from about 115% to about 135% of a diameter of the waist and wherein a diameter of the lower inflow edge is from about 105% to about 120% of the diameter of the waist, provided that the diameter of the upper inflow edge is greater than the diameter of the lower inflow edge.

4. A valve prosthesis according to claim 3, wherein the diameter of the upper inflow edge is from about 120% to about 130% of the diameter of the waist and wherein the diameter of the lower inflow edge is from about 108% to about 117% of the diameter of the waist, provided that the diameter of the upper inflow edge is greater than the diameter of the lower inflow edge.

5. A valve prosthesis according to claim 2, wherein the upper inflow edge defining a circumference and the lower inflow edge defining a circumference, wherein a diameter of the upper inflow edge is from about 105% to about 115% of a diameter of the lower inflow edge.

6. A valve prosthesis according to claim 1, wherein the frame defines a longitudinal axis, wherein the inflow portion of the frame further comprises a waist between the upper inflow portion and the lower inflow portion, wherein the upper inflow portion flares outwardly away from the longitudinal axis of the frame at an angle that is greater than an angle at which the lower inflow portion flares.

7. A valve prosthesis according to claim 6, wherein the upper inflow portion flares outwardly from the longitudinal axis of the frame at an angle from about 40° to about 60°, and wherein the lower inflow portion flares outwardly from the longitudinal axis of the frame at an angle from about 10° to about 30°.

8. A valve prosthesis according to claim 6, wherein the upper inflow portion flares outwardly from the longitudinal axis of the frame at an angle from about 45° to about 55°, and wherein the lower inflow portion flares outwardly from the longitudinal axis of the frame at an angle from about 15° to about 25°.

9. A valve prosthesis according to claim 1, wherein the inflow portion of the frame comprises a waist between the lower inflow portion and the upper inflow portion, and wherein the inflow portion comprises a plurality of closed cells, wherein each cell is connected to an adjacent cell along the waist.

10. A valve prosthesis according to claim 1, wherein the upper outflow portion is flared inwardly towards the central lumen.

11. A valve prosthesis according to claim 10, wherein the lower outflow portion and the middle outflow portion together are generally cylindrical, wherein the upper outflow portion defines an edge defining a circumference, and wherein a diameter of the edge of the upper outflow portion is from about 75% to about 97% of a diameter of the middle and lower outflow portions.

12. A valve prosthesis according to claim 11, wherein the diameter of the edge of the upper outflow portion is from about 80% to about 95% of the diameter of the middle and lower outflow portions.

13. A valve prosthesis according to claim 1, wherein the inflow portion has a waist between the lower inflow portion and the upper inflow portion, wherein the inflow portion comprises a plurality of closed cells connected along the waist, and wherein the valleys of the undulating lower outflow portion are connected to the inflow portion along the waist between the closed cells.

14. A valve prosthesis according to claim 13, wherein the valleys of the undulating lower outflow portion are connected to the inflow portion along the waist via posts.

15. A valve prosthesis according to claim 1, wherein the frame comprises a plurality of enclosed wire form cells interconnected with one another.

16. A valve prosthesis according to claim 1, wherein the frame is a self-expanding frame.

17. A valve prosthesis according to claim 1, further comprising a valve body attached to the frame.

* * * * *